United States Patent [19]

Hook et al.

[11] 4,391,985

[45] Jul. 5, 1983

[54] PROCESS FOR THE SEPARATION OF ISOPHTHALIC ACID FROM TEREPHTHALIC ACID

[75] Inventors: Richard J. Hook, Lexington, S.C.; Mark Rule, Kingsport, Tenn.

[73] Assignee: Eastman Kodak Company, Rochester, N.Y.

[21] Appl. No.: 321,948

[22] Filed: Nov. 16, 1981

[51] Int. Cl.³ .................... C07C 51/16; C07C 51/42
[52] U.S. Cl. ................................. 562/414; 562/485
[58] Field of Search ............... 562/414, 486, 485, 480; 203/47, 48

[56] References Cited

U.S. PATENT DOCUMENTS

| | | | |
|---|---|---|---|
| 2,820,819 | 1/1958 | Aroyan | 562/485 |
| 2,838,565 | 6/1958 | Heath et al. | 562/486 |
| 3,036,123 | 5/1962 | Hines et al. | 562/485 |
| 3,082,250 | 3/1963 | Baldwin et al. | 562/485 |
| 3,770,804 | 11/1973 | Nienburg et al. | 562/485 |
| 4,241,220 | 12/1980 | Itaya et al. | 562/485 |
| 4,340,752 | 7/1982 | List et al. | 562/485 |

Primary Examiner—Wilbur L. Bascomb, Jr.
Attorney, Agent, or Firm—David E. Cotey; Daniel B. Reece, III

[57] ABSTRACT

The present invention provides a process whereby by-product isophthalic acid is easily removed from terephthalic acid. The process thus provides a terephthalic acid product of improved purity. The process involves cooling at least a portion of a hot acetic acid production stream from which precipitated terephthalic acid has been removed so as to precipitate at least a portion of the isophthalic acid dissolved therein. The precipitated isophthalic acid is then removed and the production stream is recycled to a reactor from the production of terephthalic acid. The total production stream is thereby rendered unsaturated in isophthalic acid. Following the reaction in the terephthalic acid reactor, pure terephthalic acid in the substantial absence of isophthalic acid is recovered from the production stream as a precipitate. In a preferred embodiment, the cooling step involves cooling about 15 to 75%, and, at times, perhaps up to 100%, of the total hot acetic acid production stream to a temperature below about 50° C.

14 Claims, 1 Drawing Figure

PROCESS FOR THE SEPARATION OF ISOPHTHALIC ACID FROM TEREPHTHALIC ACID

BACKGROUND OF THE INVENTION

A commonly employed process for producing terephthalic acid involves the air oxidation of p-xylene in hot acetic acid, usually with a cobalt catalyst. A slurry of terephthalic acid in acetic acid is produced. The terephthalic acid precipitate is filtered off and dried, while the acetic acid filtrate is returned to the oxidizer. The terephthalic acid thus produced can be subsequently converted into polyethylene terephthalate and spun into fibers using well-known methods.

A problem associated with this process for producing terephthalic acid is that the p-xylene feed normally contains some varying amount of m-xylene, which is oxidized to isophthalic acid and is removed along with the terephthalic acid. These residual mixtures cannot be separated by fractional distillation because of the close high boiling points of isophthalic and terephthalic acids. Also, because of their high boiling points, there is the problem of decomposition and discoloration of the products. In addition, terephthalic acid has a tendency to sublime, resulting in the plugging of distillation equipment. Thus, more complicated separation procedures than simple fractionation have been proposed to separate isophthalic acid and terephthalic acid.

For example, British Patent Specification No. 970,781 discloses a method for separating isophthalic acid from terephthalic acid which comprises leaching a mixture of terephthalic acid and isophthalic acid with a solvent at an elevated temperature above the boiling point of the solvent and at a superatmospheric pressure in order to maintain the solvent in the liquid phase. An amount of solvent is employed which is sufficient to dissolve substantially all of the isophthalic acid, thereby also forming a saturated solution of the less-soluble terephthalic acid and a slurry of undissolved terephthalic acid. The slurry is thereafter thickened with respect to terephthalic acid by removing from the slurry a substantial portion of the solution containing the dissolved isophthalic acid and terephthalic acid. The thickened slurry of terephthalic acid is thereafter washed with a liquid at elevated temperature and superatmospheric pressure in order to substantially replace the remainder of the solution and to form a second slurry of solid terephthalic acid, which is thereafter separated from the second slurry. The disclosed process involves numerous process steps, thereby involving the consumption of time and energy.

U.S. Pat. No. 2,820,819 discloses that mixtures of isophthalic acid and terephthalic acid can be separated by intimately mixing the acids with liquid water at temperatures in the range of 350°–500° F. Under these conditions, a slurry is formed consisting of a concentrated solution of isophthalic acid and a solid phase which is predominantly terephthalic acid. The slurry is filtered at 350°–500° F. to obtain a filter cake, which has a substantially higher terephthalic acid content than the initial mixture, and a filtrate containing in solution a mixture of isophthalic acid and terephthalic acid having a much higher isophthalic content than the initial mixture. This process involves the utilization of elevated temperatures which require the consumption of large quantities of energy, thereby increasing the cost of production of terephthalic acid. In addition, it can be seen from the Example that the disclosed process yields a product which still contains approximately 2% isophthalic acid.

The prior art also discloses the use of extraction techniques for the separation of isophthalic and terephthalic acids. For example, U.S. Pat. No. 2,840,604 discloses a method for separating benzoic acid, isophthalic acid, and terephthalic acid which involves extraction (preferably, an initial extraction followed by a subsequent final extraction) with a solvent such as lower aliphatic alcohols, ketones, and carboxylic acids. Specific examples include methanol, ethanol, normal propanol, isopropanol, tertiary butanol, acetone, methyl ethyl ketone, diethyl ketone, methyl isobutyl ketone, formic acid, dioxane, and tetrahydrofuran.

U.S. Pat. No. 3,059,025 discloses the separation of isophthalic acid and terephthalic acid by extraction with pyridine.

U.S. Pat. No. 3,080,420 discloses a separation process whereby an ammonium solution of mixed phthalic acids is contacted with activated carbon and is then added to a solution of an acid having an ionization constant greater than that of terephthalic acid or isophthalic acid (e.g., sulfuric acid) in order to regenerate and precipitate the acid.

Unlike certain of the prior art processes discussed above, the process of the present invention does not require elevated temperatures or multiple process steps. The present invention provides an inexpensive, facile means of separating isophthalic acid from terephthalic acid, thereby yielding a terephthalic acid product of improved purity. In addition, the effect of m-xylene fluctuations in the feed to the oxidizer upon the final isophthalic content in the terephthalic acid product is strongly dampened.

SUMMARY OF THE INVENTION

The present invention provides a process for producing a terephthalic acid product of improved purity. The process comprises the steps of (a) cooling at least a portion of a hot acetic acid production stream from which precipitated terephthalic acid has been removed so as to precipitate at least a portion of the isophthalic acid dissolved therein; (b) removing the precipitated isophthalic acid and recycling the production stream to a reactor for the production of terephthalic acid, thereby rendering the total production stream unsaturated in isophthalic acid; and (c) after reaction, recovering substantially pure terephthalic acid as a precipitate from the production stream.

DESCRIPTION OF THE DRAWING

The drawing FIGURE is a schematic flow diagram which illustrates the process of the present invention.

DETAILED DESCRIPTION OF THE INVENTION

Figure 1:
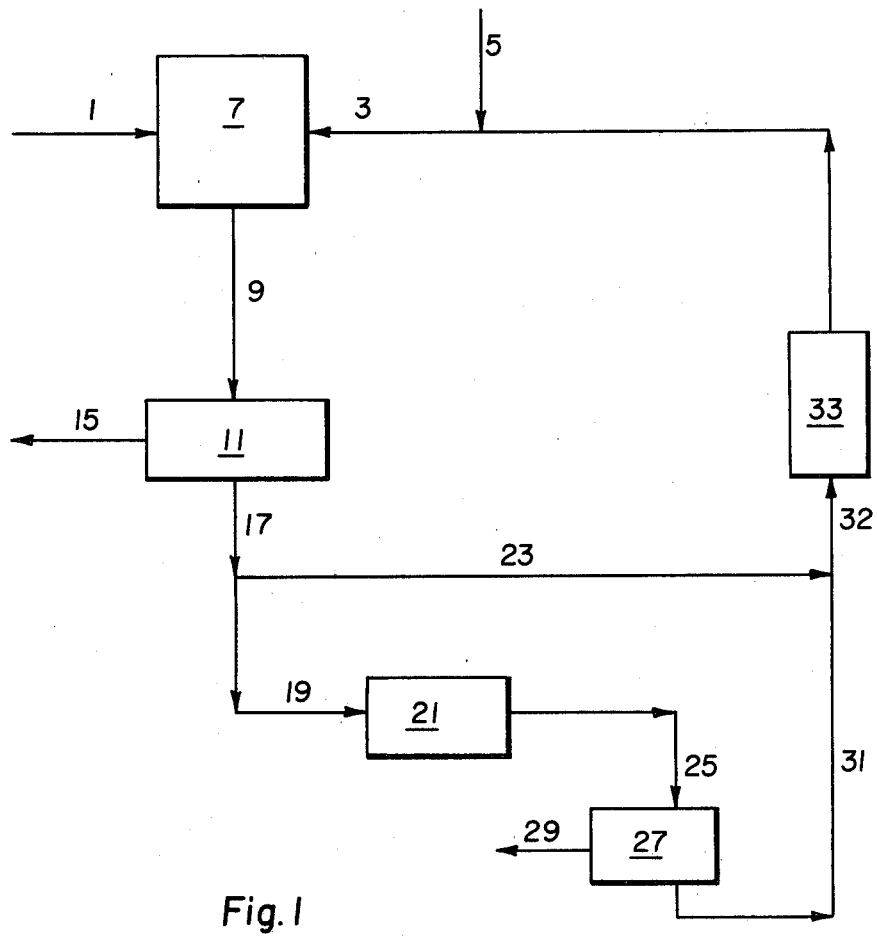

The present invention relates to an improvement in a process for producing terephthalic acid whereby p-xylene is oxidized in the presence of acetic acid to produce terephthalic acid. The p-xylene is commonly admixed with a minor amount of m-xylene impurity which is oxidized to isophthalic acid. The isophthalic acid impurity must be removed from the terephthalic acid product in order to assure the high quality of fibers spun from polyethylene terephthalate produced from the terephthalic acid. While acetic acid is generally used as the solvent in such processes for the production of terephthalic acid, other solvents, such as alcohols, methanol, ethanol, etc., and water may conceivably also be used.

According to such processes, a stream of hot (e.g., about 90°–110° C.) acetic acid, which contains the products of reaction, i.e., isophthalic acid and terephthalic acid, is fed from the oxidizing reactor to a means (such as a filter) for removing precipitated terephthalic acid. Because isophthalic acid is much more soluble in acetic acid than is terephthalic acid, the remaining filtrate contains dissolved therein a significant amount of isophthalic acid. The filtrate is usually recycled to the oxidizing reactor where additional p-xylene, with m-xylene impurity therein, is added to the stream and oxidized. The product stream is then filtered and recycled as before. Thus, the acetic acid soon becomes saturated in isophthalic acid as well as terephthalic acid, so that a minor amount of isophthalic acid is precipitated along with the product terephthalic acid.

The process of the present invention is based upon the recognition that isophthalic acid is normally co-precipitated with the terephthalic acid product only because the acetic acid stream is saturated with isophthalic acid at the filtration temperature. The process of the present invention achieves the production of a pure terephthalic acid product by maintaining the acetic acid production stream unsaturated in isophthalic acid.

The process of the present invention involves cooling at least a portion of the hot acetic acid production stream from which precipitated terephthalic acid has been removed (i.e., the primary filtrate) so as to precipitate at least a portion of the isophthalic acid dissolved therein. The hot acetic acid production stream following removal of terephthalic acid product (e.g., by filtration) is commonly at a temperature within the range of 90°–110° C., e.g., about 95° C. The acetic acid production stream is cooled to a temperature at which at least a portion of the isophthalic acid dissolved therein will precipitate. Typically, the hot acetic acid production stream is cooled to a temperature less than about 70° C., for example, a temperature of about 40°–70° C. Preferably, the hot acetic acid production stream is cooled to a temperature of about 50° C.

After cooling, precipitated isophthalic acid is removed from the acetic acid production stream, e.g., by filtration ("secondary filtration"). The cooled acetic acid stream is then recycled to a reactor for the production of terephthalic acid. The term "recycle" as used herein includes the steps of recombining the treated portion of the production stream with any untreated portion of the production stream and reheating the total stream to a temperature appropriate for reaction. The removal of precipitated isophthalic acid thereby renders the total production stream unsaturated in isophthalic acid. The acetic acid production stream is therefore able to dissolve the isophthalic acid which is produced from any m-xylene impurity which may be present in the feed to the reactor.

As suggested above, only a portion of the acetic acid production stream which is collected as filtrate after the removal of terephthalic acid product need be treated as described above. That portion which is not so treated can be recycled directly to the oxidizing reactor. That portion of the acetic acid production stream to be treated can be readily determined by one of ordinary skill in the art based upon such factors as the economics of the particular process, the amount of m-xylene present in the feed to the reactor (and thus the amount of isophthalic acid which must be removed in order to maintain an acetic acid solution unsaturated in isophthalic acid), etc. Commonly, at least 15% of the acetic acid production stream will be treated as described above. Preferably, about 15–75% of the acetic acid production stream will be so treated, and, at times, it may be desirable to treat the entire acetic acid production stream.

The acetic acid production stream which is recycled to the reactor is then utilized as solvent during the reaction. After reaction, the hot acetic acid production stream containing precipitated terephthalic acid is again filtered as before. This time, however, because the acetic acid production stream fed to the reactor was unsaturated in isophthalic acid, any isophthalic acid produced during the reaction can be dissolved by the acetic acid, and no isophthalic acid is precipitated. Thus, a substantially pure terephthalic acid product is recovered.

Those conditions which are necessary to maintain an acetic acid production stream which is unsaturated in isophthalic acid will vary with the content of m-xylene impurity in the feed and will be apparent to one of ordinary skill in the art. Should the removal of increased amounts of isophthalic acid be necessary, it will be apparent that the same can be accomplished by further decreasing the temperature of the secondary filtration and/or increasing the proportion of the total acetic acid production stream which is subjected to the low temperature, secondary filtration. Conversely, should the purity of the feed improve so that the removal of less isophthalic acid is required, the temperature of the secondary filtration can be increased and/or that proportion of the total production stream to be treated can be decreased.

In an exemplary process, after the primary filtration in which terephthalic acid product is removed, about 20% of the acetic acid production stream is cooled to about 50° C. Isophthalic acid is allowed to precipitate, and the stream is then filtered, removing the precipitated isophthalic acid. That portion of the production stream so treated is then recombined with the untreated production stream, and the total production stream is reheated to an appropriate temperature (e.g., about 90°–110° C.). The total production stream is thereby rendered about 80–90% saturated in isophthalic acid and is therefore capable of dissolving the isophthalic acid which is produced by the oxidation of a p-xylene stream containing typical amounts of m-xylene impurity. The precipitated terephthalic acid formed during the reaction is therefore recovered free of isophthalic acid, and the incremental amount of isophthalic acid added to the system is removed in the subsequent secondary filtration.

In order to further illustrate the process of the present invention, reference is made to the drawing. A feed stream 1 of p-xylene containing minor amounts of m-xylene is fed to reaction zone 7. Also supplied to reaction zone 7 is acetic acid feed stream 3. Preferably, acetic acid feed stream 3 contains at least some fresh acetic acid (provided by line 5) together with recycled acetic acid. After oxidation of the xylene isomers in reaction zone 7 by known processes, the product stream 9 containing terephthalic acid, isophthalic acid, acetic acid, and reaction by-products is fed to filtration zone 11. Substantially pure terephthalic acid is separated from the product stream and is removed from filtration zone 11 by way of line 15. The filtrate is then removed by way of line 17. At least a portion of the filtrate is fed by way of line 19 to cooling zone 21. The remainder of the filtrate, if any, is recycled by way of line 23. From cooling zone 21, the remaining filtrate is fed by way of line 25 to a second filtration zone 27. In the second filtration zone 27, precipitated isophthalic acid is removed by way of line 29, and the remaining filtrate is recycled by way of line 31. The total production stream is thereby rendered unsaturated in isophthalic acid. Recycle streams 31 and 23 are then combined and fed by way of line 32 to heating zone 33 and the recycle stream is then fed by way of line 3 back to reaction zone 7.

The process of the present invention thus allows the preparation of terephthalic acid essentially free of isophthalic acid. Wide variations in the level of isophthalic acid present in the system can be tolerated as long as the acetic acid production stream does not become saturated. Only a portion of the acetic acid stream need be treated according to the process of the present invention in order for the advantages of the present process to be realized. The process of the present invention thus improves the quality and uniformity of terephthalic acid produced by the oxidation of p-xylene in the presence of m-xylene impurity.

This invention will be further illustrated by the following Example although it will be understood that this Example is included merely for purposes of illustration and is not intended to limit the scope of the invention.

EXAMPLE 1

Acetic acid at 100° C. was saturated with isophthalic acid and then slurried with 20 grams of terephthalic acid containing 1% isophthalic acid. The slurry was filtered at 95° C., and the precipitate was collected (Sample No. 1). The filtrate was cooled to 50° C. and refiltered. The precipitate was collected as Sample No. 2. The filtrate was then reheated to 95° C., slurried with another 20 grams of terephthalic acid containing 1% isophthalic acid, and the process was repeated, yielding Sample Nos. 3 and 4. The results are summarized in Table I.

TABLE I

| Sample No. | Filtration Temp. (°C.) | Wt. Solids (Grams) | Mole % IPA | Mole % TPA |
| --- | --- | --- | --- | --- |
| 1 | 95 | 20.23 | 6.52 | 93.48 |
| 2 | 50 | 0.67 | 94.95 | 5.05 |
| 3 | 95 | 19.87 | 0 | 100 |
| 4 | 50 | 0.20 | 85.52 | 14.84 |

The results of the analyses of the isophthalic acid and terephthalic acid content of the collected precipitates demonstrate that the secondary filtration was completely effective in removing isophthalic acid from terephthalic acid.

The invention has been described in detail with particular reference to preferred embodiments thereof, but it will be understood that variations and modifications can be effected within the spirit and scope of the invention.

We claim:

1. A process for producing a terephthalic acid product of improved purity, said process comprising the steps of
   (a) cooling at least a portion of a hot acetic acid production stream from which precipitated terephthalic acid has been removed so as to precipitate at least a portion of the isophthalic acid dissolved therein;
   (b) removing the precipitated isophthalic acid and recycling said production stream to a reactor for the production of terephthalic acid, thereby rendering the total production stream unsaturated in isophthalic acid; and
   (c) after reaction, recovering substantially pure terephthalic acid as a precipitate from said production stream.

2. The process of claim 1 wherein said portion of a hot acetic acid production stream comprises at least about 15% of the total hot acetic acid production stream.

3. The process of claim 1 wherein said portion of a hot acetic acid production stream is cooled to a temperature below about 70° C.

4. The process of claim 3 wherein said portion of a hot acetic acid production stream is cooled to a temperature of about 40° to 70° C.

5. The process of claim 4 wherein said portion of a hot acetic acid production stream is cooled to a temperature of about 50° C.

6. The process of claim 1 wherein said total production stream is rendered about 80 to 90% saturated in isophthalic acid.

7. A process for producing a terephthalic acid product of improved purity, said process comprising the steps of:
   (a) cooling to about 50° C. at least about 15% of a hot acetic acid production stream from which precipitated terephthalic acid has been removed so as to precipitate isophthalic acid;
   (b) removing the isophthalic acid and recycling said production stream to a reactor for the production of terephthalic acid, thereby rendering said production stream about 80 to 90% saturated in isophthalic acid; and
   (c) after reaction, removing substantially pure terephthalic acid as a precipitate from said production stream.

8. In a process for producing terephthalic acid which comprises oxidizing p-xylene in admixture with a minor amount of m-xylene impurity in the presence of hot acetic acid, subsequently removing precipitated terephthalic acid in admixture with a minor amount of precipitated isophthalic acid, and thereafter recycling said acetic acid, the improvement comprising:
   (a) cooling at least a portion of the hot acetic acid production stream from which precipitated terephthalic acid has been removed so as to precipitate at least a portion of the isophthalic acid remaining dissolved therein,
   (b) removing the precipitated isophthalic acid, and recycling said production stream to a reactor for the production of terephthalic acid, thereby rendering the total production stream unsaturated in isophthalic acid; and
   (c) after reaction, recovering substantially pure terephthalic acid as a precipitate from said production stream.

9. The process of claim 8 wherein said portion of a hot acetic acid production stream comprises at least about 15% of the total hot acetic acid production stream.

10. The process of claim 8 wherein said portion of a hot acetic acid production stream is cooled to a temperature below about 70° C.

11. The process of claim 10 wherein said portion of a hot acetic acid production stream is cooled to a temperature of about 40° to 70° C.

12. The process of claim 11 wherein said portion of a hot acetic acid production stream is cooled to a temperature of about 50° C.

13. The process of claim 8 wherein said total production stream is rendered about 80 to 90% saturated in isophthalic acid.

14. In a process for producing terephthalic acid which comprises oxidizing p-xylene in admixture with a minor amount of m-xylene impurity in the presence of hot acetic acid, subsequently removing precipitated terephthalic acid in admixture with a minor amount of precipitated isophthalic acid, and thereafter recycling said acetic acid, the improvement comprising:

(a) cooling to about 50° C. at least about 15% of said hot acetic acid production stream from which precipitated terephthalic acid has been removed so as to precipitate isophthalic acid;

(b) removing the isophthalic acid and recycling said production stream to a reactor for the production of terephthalic acid, thereby rendering said production stream about 80 to 90% saturated in isophthalic acid; and (c) after reaction, removing substantially pure terephthalic acid as a precipitate from said production stream.

* * * * *